United States Patent
Brander et al.

(10) Patent No.: US 9,867,550 B2
(45) Date of Patent: *Jan. 16, 2018

(54) METHOD AND APPARATUS FOR LOCATING PASSIVE INTEGRATED TRANSPONDER TAGS

(71) Applicant: Health Beacons, Inc., The Woodlands, TX (US)

(72) Inventors: Christopher Brander, Salisbury (AU); Robert Petcavich, The Woodlands, TX (US); Murray Reicher, Rancho Santa Fe, CA (US)

(73) Assignee: Health Beacons, Inc., Concord, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/642,217

(22) Filed: Mar. 9, 2015

(65) Prior Publication Data
US 2015/0264891 A1 Sep. 24, 2015

Related U.S. Application Data

(63) Continuation of application No. 12/371,048, filed on Feb. 13, 2009, now Pat. No. 8,973,584.

(51) Int. Cl.
*A61B 5/06* (2006.01)
*G06K 7/00* (2006.01)
(Continued)

(52) U.S. Cl.
CPC .............. *A61B 5/06* (2013.01); *A01K 11/006* (2013.01); *A61B 90/39* (2016.02); *G06K 7/0008* (2013.01);
(Continued)

(58) Field of Classification Search
CPC ... A61B 19/44; A61B 19/54; A61B 2019/488; A61B 2019/5251; A61B 2019/547;
(Continued)

(56) References Cited

U.S. PATENT DOCUMENTS

| 4,142,530 A | 3/1979 | Wittkampf |
| 4,592,356 A | 6/1986 | Gutierrez |

(Continued)

FOREIGN PATENT DOCUMENTS

| EP | 0967927 B1 | 4/2003 |
| WO | WO 1996/022058 | 7/1996 |

(Continued)

OTHER PUBLICATIONS

"p-Chips for Life Science and Diagnostic Applications"; http://www.pharmaseq.com/index.php/technology/pchipsforlifesciencediagnosticapplications; printed Jan. 2014; PharmaSeq, Inc.; 1 page.

(Continued)

*Primary Examiner* — Charles A Marmor, II
*Assistant Examiner* — Carrie R Dorna
(74) *Attorney, Agent, or Firm* — Knobbe, Martens, Olson & Bear LLP (57) ABSTRACT

An apparatus for locating an embedded passive integrated transponder (PIT) tag is provided. An embodiment of the locating apparatus includes a resonator capable of electromagnetically coupling to the PIT tag, and a feedback circuit connected to the resonator and configured to monitor a load conductance of the resonator. A distance between the resonator and the PIT tag is indicated by a change in the monitored load conductance when the resonator and the PIT tag are electromagnetically coupled. Another embodiment includes a resonator capable of stimulating a response signal from a PIT tag, and a processing circuit capable of calcu- (Continued)

lating the distance between the resonator and the PIT tag based on the amplitude of the response signal.

6 Claims, 7 Drawing Sheets

(51) Int. Cl.
  *A01K 11/00* (2006.01)
  *G06K 7/10* (2006.01)
  *A61B 90/00* (2016.01)
(52) U.S. Cl.
  CPC ..... *G06K 7/10297* (2013.01); *G06K 7/10386* (2013.01); *A61B 2090/397* (2016.02); *G06K 2007/10524* (2013.01)
(58) Field of Classification Search
  CPC ........... A61B 5/055; A61B 5/06; A61B 5/061; A61B 5/064; A61B 5/065
  See application file for complete search history.

(56) References Cited

U.S. PATENT DOCUMENTS

| | | |
|---|---|---|
| 4,809,713 A | 3/1989 | Grayzel |
| 4,874,375 A | 10/1989 | Ellison |
| 4,886,049 A | 12/1989 | Darras |
| 5,011,473 A | 4/1991 | Gatturna |
| 5,059,197 A | 10/1991 | Urie et al. |
| 5,099,845 A | 3/1992 | Besz et al. |
| 5,127,916 A | 7/1992 | Spencer et al. |
| 5,158,084 A | 10/1992 | Ghiatas |
| 5,197,482 A | 3/1993 | Rank |
| 5,221,269 A | 6/1993 | Miller et al. |
| 5,284,128 A | 2/1994 | Hart |
| 5,325,873 A | 7/1994 | Hirschi et al. |
| 5,409,004 A | 4/1995 | Sloan |
| 5,709,697 A | 1/1998 | Ratcliff et al. |
| 5,864,323 A | 1/1999 | Berthon |
| 5,952,935 A | 9/1999 | Mejia et al. |
| 5,967,968 A | 10/1999 | Nishioka |
| 5,977,431 A | 11/1999 | Knapp et al. |
| 5,989,265 A | 11/1999 | Bouquet De La Joliniere et al. |
| 6,018,094 A | 1/2000 | Fox |
| 6,026,818 A | 2/2000 | Blair et al. |
| 6,161,034 A | 12/2000 | Burbank et al. |
| 6,173,715 B1 | 1/2001 | Sinanan et al. |
| 6,184,777 B1 | 2/2001 | Mejia |
| 6,239,724 B1 | 5/2001 | Doron et al. |
| 6,261,247 B1 | 7/2001 | Ishikawa et al. |
| 6,363,940 B1 | 4/2002 | Krag |
| 6,398,710 B1 | 6/2002 | Ishikawa et al. |
| 6,402,037 B1 | 6/2002 | Prasad et al. |
| 6,427,081 B1 | 7/2002 | Burbank et al. |
| 6,443,980 B1 | 9/2002 | Wang et al. |
| 6,496,717 B2 | 12/2002 | Cox et al. |
| 6,567,689 B2 | 5/2003 | Burbank et al. |
| 6,611,141 B1 | 8/2003 | Schulz et al. |
| 6,698,433 B2 | 3/2004 | Krag |
| 6,995,729 B2 | 2/2006 | Govari et al. |
| 7,026,941 B1 | 4/2006 | Anderson |
| 7,195,629 B2 | 3/2007 | Behl et al. |
| 8,113,210 B2 | 2/2012 | Petcavich et al. |
| 8,457,757 B2 | 6/2013 | Cauller et al. |
| 8,353,917 B2 | 10/2013 | Mandecki et al. |
| 8,939,153 B1 | 1/2015 | Reicher et al. |
| 8,973,584 B2 | 3/2015 | Brander et al. |
| 9,198,654 B1 | 12/2015 | Reicher et al. |
| 2001/0020148 A1 | 9/2001 | Sasse et al. |
| 2002/0046756 A1 | 4/2002 | Laizzo et al. |
| 2002/0107445 A1 | 8/2002 | Govari |
| 2002/0138009 A1 | 9/2002 | Brockway et al. |
| 2002/0170591 A1 | 11/2002 | Armer et al. |
| 2003/0004411 A1 | 1/2003 | Govari et al. |
| 2003/0018246 A1 | 1/2003 | Govari et al. |
| 2003/0018353 A1 | 1/2003 | Yang et al. |
| 2003/0023161 A1 | 1/2003 | Govari et al. |
| 2003/0062988 A1 | 4/2003 | Mandecki et al. |
| 2003/0063351 A1 | 4/2003 | Mandecki et al. |
| 2003/0120150 A1 | 6/2003 | Govari |
| 2004/0030379 A1 | 2/2004 | Hamm et al. |
| 2004/0087914 A1 | 5/2004 | Bryan et al. |
| 2004/0092965 A1 | 5/2004 | Parihar |
| 2004/0236193 A1 | 11/2004 | Sharf |
| 2005/0033108 A1 | 2/2005 | Sawyer |
| 2005/0099290 A1 | 5/2005 | Govari |
| 2005/0137652 A1 | 6/2005 | Cauller et al. |
| 2005/0159789 A1 | 7/2005 | Brockway et al. |
| 2005/0165305 A1 | 7/2005 | Foerster et al. |
| 2005/0231330 A1 | 10/2005 | Drews et al. |
| 2005/0242177 A1 | 11/2005 | Roberge et al. |
| 2005/0272977 A1 | 12/2005 | Saadat et al. |
| 2006/0063962 A1 | 3/2006 | Drobnik et al. |
| 2006/0079793 A1 | 4/2006 | Mann |
| 2006/0084865 A1 | 4/2006 | Burbank et al. |
| 2006/0097847 A1 | 5/2006 | Bervoets et al. |
| 2006/0117859 A1 | 6/2006 | Liu et al. |
| 2006/0155190 A1 | 7/2006 | Burbank et al. |
| 2006/0184396 A1 | 8/2006 | Dennis et al. |
| 2006/0208896 A1 | 9/2006 | Mason |
| 2006/0241396 A1 | 10/2006 | Fabian et al. |
| 2006/0258933 A1 | 11/2006 | Ellis et al. |
| 2006/0271096 A1 | 11/2006 | Hamada |
| 2007/0016009 A1 | 1/2007 | Lakin et al. |
| 2007/0135803 A1 | 6/2007 | Belson |
| 2007/0225544 A1 | 9/2007 | Vance et al. |
| 2007/0249901 A1 | 10/2007 | Ohline et al. |
| 2008/0086046 A1 | 4/2008 | Petcavich et al. |
| 2008/0281190 A1 | 11/2008 | Petcavich et al. |
| 2009/0005677 A1 | 1/2009 | Weber et al. |
| 2009/0081461 A1 | 3/2009 | Yi et al. |
| 2009/0131825 A1 | 5/2009 | Burbank et al. |
| 2009/0157147 A1 | 6/2009 | Cauller et al. |
| 2009/0157151 A1 | 6/2009 | Cauller et al. |
| 2009/0198293 A1 | 8/2009 | Cauller et al. |
| 2010/0023093 A1 | 1/2010 | Govari |
| 2010/0268015 A1 | 10/2010 | Drobnik et al. |
| 2011/0071362 A1 | 3/2011 | Reicher |
| 2011/0071387 A1 | 3/2011 | Petcavich et al. |
| 2011/0077659 A1 | 3/2011 | Mandecki et al. |
| 2012/0277752 A1 | 11/2012 | Wasielewski |
| 2013/0268029 A1 | 10/2013 | Cauller et al. |
| 2014/0018663 A1 | 1/2014 | Harmer et al. |
| 2014/0106470 A1 | 4/2014 | Kopacka et al. |
| 2016/0051164 A1 | 2/2016 | Derichs et al. |

FOREIGN PATENT DOCUMENTS

| | | | |
|---|---|---|---|
| WO | WO 98/30166 | | 7/1998 |
| WO | WO 2007/087447 | * | 8/2007 |
| WO | WO 2007/117478 | | 10/2007 |
| WO | WO 2009/070697 | | 6/2009 |
| WO | WO 2016/032910 | | 3/2016 |

OTHER PUBLICATIONS

"Tagging of Laboratory Mice Using Electronic p-Chips", Pharmaseq, Inc. White Paper; www.pharmaseq.com; 2012; accessed Jan. 2014; 8 pages.

Reicher, Joshua et al.; "Use of Radio Frequency Identification (RFID) Tags in Bedside Monitoring of Endotracheal Tube Position"; Journal of Clinical Monitoring and Computing, Jun. 2007;21:155-8; reformatted into 5 pages.

Reicher, Joshua et al.; "Radiofrequency Identification Tags for Preoperative Tumor Localization: Proof of Concept", Women's Imaging Original Research; Nov. 2008; pp. 1359-1365.

Written Opinion of the International Searching Authority in International Application No. PCT/US2015/046409, dated Nov. 27, 2015.

Ozyagcilar, Talat. "Implementing a Tilt-Compensated eCompass using Accelerometer and Magnetometer Sensors." http://cache.

(56) References Cited

OTHER PUBLICATIONS freescale.com/files/sensors/doc/app_note/AN4248.pdf. Freescale Semiconductor, Nov. 2015, pp. 1-21, Rev. 4.0 Document No. AN4248.
Ozyagcilar, Talat. "Layout Recommendations for PCBs Using a Magnetometer Sensor." http://cache.freescale.com/files/sensors/doc/app_note/AN4247.PDF. Freescale Semiconductor, Nov. 2015, pp. 1-13, Rev. 4.0, Documents No. AN4247.
Ozyagcilar, Talat. "Calibrating an eCompass in the Presence of Hard-and Soft-Iron Interference." http://cache.freescale.com/files/sensors/doc/app_note/PDF. Freescale Semiconductor, Nov. 2015, pp. 1-18, Rev. 4.0, Documents No. AN4246.
http:www.vectomav.com/support/library/magnetometer. VectorNav Technologies, LLC, printed on Jul. 29, 2015.

* cited by examiner

METHOD AND APPARATUS FOR LOCATING PASSIVE INTEGRATED TRANSPONDER TAGS

BACKGROUND

The present invention relates generally to location devices and more specifically to methods and apparatus used to locate passive integrated transponder tags (hereinafter "PIT tags").

Location devices, such as metal detectors and radio frequency transponder locators for tracking objects or specimens such as animals are known in the art. However, these devices have drawbacks that make them unsuitable for some tasks. For example, radio frequency transponder tags are intended for location and tracking of objects or animals at comparatively long range, and not for close-range location of small objects with great precision. Metal detectors react to any substantial amount of metal found within an object, and therefore do not differentiate between PIT tags and metal objects, or multiple devices embedded in a single object. They are also incapable of the precision required for certain applications. Thus, when it is necessary to identify a location of a single embedded device to within a few millimeters, and/or it is desirable to differentiate between multiple implanted devices, PIT tags are preferred.

PIT tags have been used for many years to identify specimens, including livestock, domestic pets, birds, fish, and other marine animals for various management and/or research purposes. Each PIT tag generally includes a small ferrite-cored coil attached to a microchip. The microchip has a capacitor that causes the coil to resonate at a predetermined frequency when energized and circuitry to generate and transmit a coded identification number or message in response to a received interrogation signal which energizes the coil. PIT tags do not contain an internal energy source. Instead, energy needed to transmit the coded identification number is obtained through electromagnetic coupling, which causes a transfer of energy from a powered device to the PIT tag. Typically, the PIT tag is enclosed in a glass covering or envelope about 2 mm in diameter and about 11 mm in length, although other packaging is possible. PIT tags are usually injected up to a few centimeters below the outer surface of an object or the specimen's skin using a hypodermic syringe, but other methods of attachment, for example ear tags, are also known.

Protocols for a PIT tag interrogation and messaging system include those defined by International Standards Organization (ISO) standards 11784 and 11785, and other protocols that have been introduced by various manufacturers. PIT tags may be either half-duplex (HDX) or full-duplex (FDX). An HDX PIT tag receives a pulsed interrogation signal from a "PIT tag reader" and then responds with a coded identification number. An FDX PIT tag continuously transmits a coded identification number while receiving an interrogation signal, which may be either pulsed or continuous. PIT tags are typically read at close range, generally well under 1 meter, and often less than a few centimeters.

In many applications, the embedded PIT tags remain in position for the life of the specimen or object and are treated as disposable items. One known limitation of PIT tag readers, which are devices that are capable of receiving the coded identification number transmitted by the PIT tag and displaying the number, is that the readers cannot accurately determine the position of the PIT tag after it has been embedded within an object or specimen. However, in certain situations it is beneficial to be able to accurately determine the location of the PIT tag in terms of the depth of the PIT tag relative to the object's surface and/or the location on the surface of the object below which the PIT tag is embedded. For example, knowing the exact position of a PIT tag is helpful to reduce damage to an object or specimen if it is necessary to remove the PIT tag from the object or specimen. Knowledge of a PIT tag's position is also beneficial if the location of the PIT tag is used as a marker for some other device having the PIT tag attached or adjacent thereto and which is also disposed in the object or specimen. Thus, there is a need for a PIT tag locating device that is able to determine the position and depth of a PIT tag that has been embedded in an object or specimen in addition to receiving a coded identification number transmitted by the PIT tag.

SUMMARY

A locating apparatus for locating a passive integrated transponder (PIT) tag responds to the above-identified need for improved PIT tag locating. The locating apparatus allows a user to pass a device over the outer surface of an object or the skin of a specimen to locate an embedded PIT tag with improved precision relative to conventional techniques. The improved precision reduces the need for guesswork and/or exploratory cutting by the device user to locate the PIT tag.

In one embodiment of the invention, an apparatus for locating an embedded passive integrated transponder (PIT) tag is provided. The locating apparatus includes a resonator capable of electromagnetically coupling to the PIT tag, and a feedback circuit connected to the resonator and configured to monitor a load conductance of the resonator. A distance D between the resonator and the PIT tag is indicated by a change in the monitored load conductance when the resonator and the PIT tag are electromagnetically coupled.

In another embodiment, an apparatus for locating an embedded PIT tag includes a resonator capable of electromagnetically coupling to the PIT tag and outputting an interrogating signal. The locating apparatus also has a drive circuit configured to drive said resonator to stimulate a response signal from the PIT tag, the response signal being superimposed over the interrogating signal in the resonator. Also included are a demodulator configured to demodulate the combined interrogating signal and response signal output from the resonator, and a bandpass amplifier configured to receive an output of the demodulator and isolate and amplify the response signal. Finally, the locating apparatus includes a peak detector configured to measure at least an amplitude of the amplified response signal, where the amplitude is a function of a distance D between the resonator and the PIT tag.

A method for locating a PIT tag embedded in an object includes steps of providing an energized locating apparatus having a search coil and an indicator, and placing said search coil directly adjacent to an outer surface of the object such that the search coil electromagnetically couples to and identifies the PIT tag. Once the search coil and the PIT tag are electromagnetically coupled, the apparatus displays an indication value that indicates a distance between the search coil and the PIT tag. The search coil is then repositioned on the outer surface of the object to obtain a new indication value until the indication value reaches a maximum. The indicator displays a maximum indication value when the distance between the search coil and the PIT tag is at a minimum.

The foregoing and other advantages of the invention will become apparent to those of reasonable skill in the art from the following detailed description as considered in conjunction with the accompanying drawings.

DETAILED DESCRIPTION

The following is a detailed description of certain embodiments of the invention presently contemplated by the inventor to be the best mode of carrying out his invention.

Passive integrated transponder (PIT) tags are useful for providing ID information about a particular PIT tag that is embedded in a body or specimen. In the particular embodiments that are discussed hereinbelow, an actual physical location of a PIT tag within the object or specimen can be determined by using an apparatus for locating a PIT tag. Additionally, a coded identification number transmitted by the PIT tag can optionally be read. In particular, an embodiment of the apparatus uses electromagnetic coupling to change load conductance on an oscillator, which is measured and output to an accessory to provide an audio and/or video indication to a user. In this manner, the user can determine the position of the PIT tag embedded within the object or specimen, including the depth of the PIT tag relative to the outer surface of the object. This improved locating apparatus reduces the need for exploratory surgery or other locating methods to determine the location of the PIT tag within the object or under the skin of the specimen. For simplicity, present embodiments of the invention will contemplate a PIT tag implanted under a specimen's skin.

When a passive resonator, such as a PIT tag, is brought near a driven resonator or oscillator, electromagnetic coupling causes a transfer of energy. The exact amount of energy transferred depends upon the resonant frequencies of the two resonators (or resonator and oscillator), as well as the distance between them and their relative orientation.

Figure 1A:
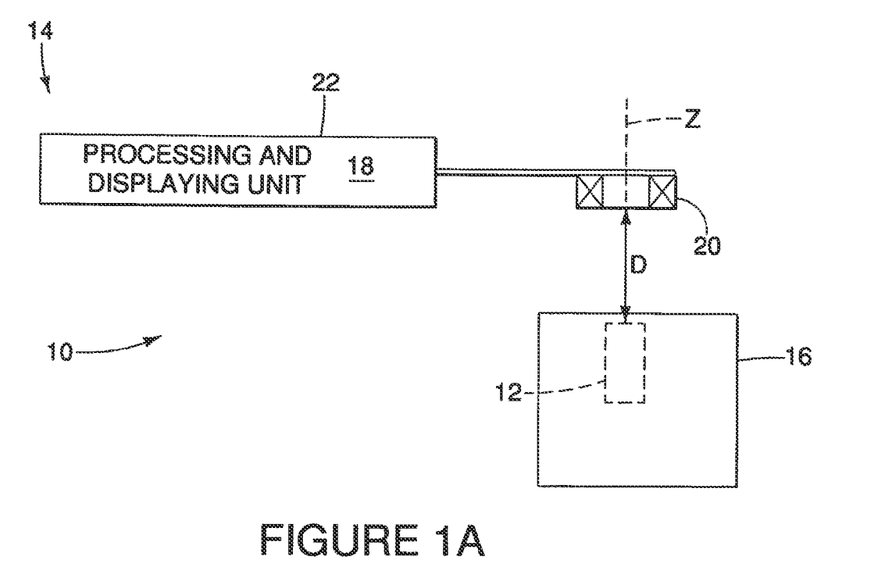
FIG. 1A is a side view of a locating system.
Figure 1B:
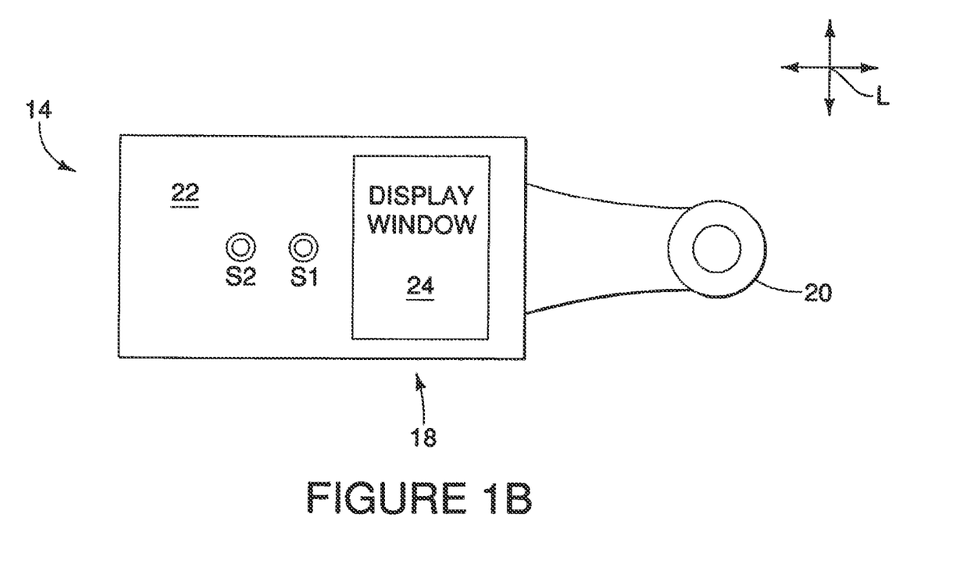
FIG. 1B is an overhead plan view of the PIT tag locating apparatus of the locating system of FIG. 1A.

Referring now to FIGS. 1A and 1B, a locating system is generally designated 10. The locating system includes a transponder, such as a PIT tag 12, and a transceiver, such as a PIT tag locating apparatus 14. The PIT tag 12 is configured to be implanted under the skin of a specimen 16. The PIT tag 12 is further capable of transmitting a response signal when energized by an interrogating signal or electromagnetically coupled to a driven coil such as the coil in the locating apparatus 14.

An embodiment of the PIT tag locating apparatus 14 includes a processing and display unit 18 for analyzing data such as a load conductance on the locating apparatus, strength of a signal emitted by the transponder, and optionally encoded content of a message incorporated in this signal. The locating apparatus 14 also includes a search coil 20, which is preferably annular or solenoidal in shape, attached to the processing and display unit 18. The search coil 20 can be driven at a pre-selected frequency substantially equal to the natural resonant frequency of a PIT tag 12. The processing and display unit 18 is housed in a hand-held case 22 that defines a display window 24. The display window 24 allows a user to view distance and/or PIT tag identification number information. The PIT tag locating apparatus 14 measures a distance D between the search coil 20 and the PIT tag 12 when the search coil 20 is energized due to electromagnetic coupling to the PIT tag 12.

The search coil 20 preferably has an outer diameter of approximately 30 millimeters and an inner diameter of approximately 17 millimeters. The search coil 20 may however be larger or smaller as appropriate to the expected depth of the PIT tag 12 and the detection range required. As indicated in FIG. 1B, which is a top view of the PIT tag locating apparatus 14 of FIG. 1A, the search coil 20 may be moved laterally (i.e., in any of the directions indicated by the arrows L) over the skin of the specimen 16 at a small distance above the skin or at the surface thereof to determine the lateral position of a PIT tag 12 implanted within the specimen. Once the lateral position of the PIT tag 12 is known, the search coil 20 can be lowered to contact the skin of the specimen 16 to determine the depth at which the PIT tag 12 was implanted, which is calculated by the processing and display unit 18 based upon (i) the change in load conductance when there is electromagnetic coupling between the locating apparatus 14 and the PIT tag, or (ii) the strength of the transponded signal received from the PIT tag, and the depth can be viewed via the display window 24.

It will be appreciated by those of skill in the art that the measured data displayed by the PIT tag locating apparatus 14 will depend upon the size, shape, and orientation of the search coil 20 in relation to the PIT tag 12, as well as the distance D between the PIT tag and the search coil. For example, considering the magnetic flux distribution surrounding the search coil 20, one skilled in the art can appreciate that the maximum generated response for a PIT tag 12 that is oriented parallel to a center axis Z of the search coil will occur when the center of the search coil is directly over the center of the PIT tag. A PIT tag 12 that is oriented obliquely relative to the center axis Z of the search coil 20 will generate a maximum response when the PIT tag is slightly off-center relative to the center axis Z of the search coil, and a horizontal PIT tag (i.e., a PIT tag oriented perpendicular to the center axis of the search coil) will generate two maxima of positions a little to either side of center of the PIT tag, with lower values in between the two maxima. Thus, it should be noted that the effects of orientation, as well as other factors, limit the ability to obtain an exact measurement of the depth and lateral position of a PIT tag 12 implanted in a specimen 16. However, measurements obtained using the PIT tag locating apparatus 14 are generally accurate within a few millimeters both in lateral position and in depth.

It will also be apparent that a calibration procedure should be performed in order to select suitable algorithms to correctly relate the output audio or visual display, for instance a range of tones, a bar-graph or a numerical readout, to the distance D between the PIT tag 12 and the search coil 20. It is contemplated that one or more sets of calibration data could be included to suit PIT tags of different characteristics.

In most applications, the PIT tag 12 will be at least nearly parallel to the center axis Z of the search coil 20. Thus, when the PIT tag locating apparatus 14 indicates that distance between the PIT tag 12 and the search coil 20 is at a minimum (i.e., the lateral position of the PIT tag is found), the locating apparatus will also indicate the approximate vertical placement of the PIT tag. In the embodiments shown and described herein, the distance scale used for determining vertical placement has been calibrated for vertical PIT tags, and will be slightly less accurate for oblique PIT tags that are offset relative to the center axis Z of the search coil 20. For PIT tags 12 that are oriented perpendicular to the center axis Z of the search coil 20, a different scale is preferably implemented to take into account the dual maxima when a determination of the vertical placement is desired.

Figure 2:
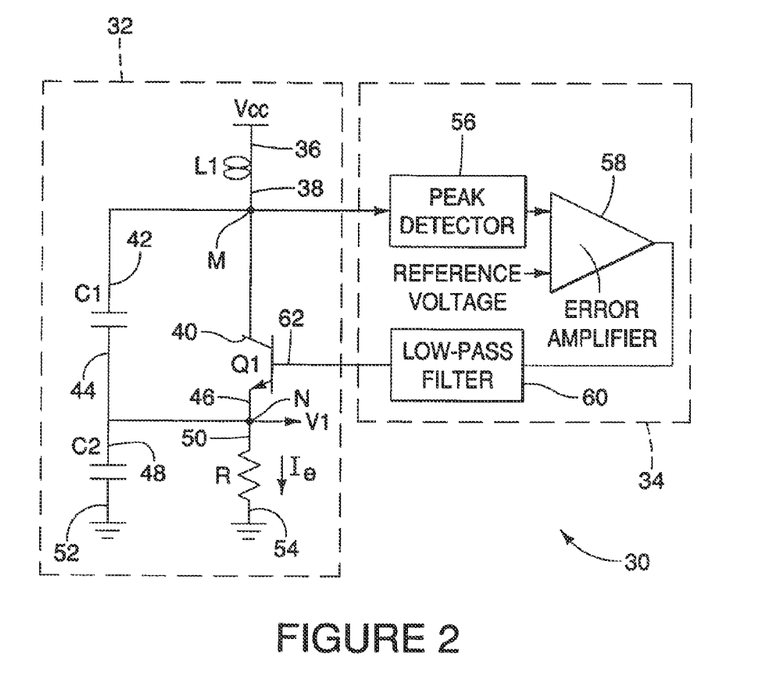
FIG. 2 is a block diagram of an exemplary circuit used in the PIT tag locating apparatus of FIG. 1B.

Referring now to FIG. 2 a first example of a PIT tag locator circuit is generally designated 30. The PIT tag locator circuit 30 is used in a transceiver such as the PIT tag locating apparatus 14, and can be used to locate transponders such as PIT tags 12 that have been implanted under a specimen's skin. The PIT tag locator circuit 30 is formed by an oscillator 32 (shown in dashed lines) connected to a feedback circuit 34 (shown in dashed lines). The oscillator 32 is made up of an inductor L1, two capacitors C1, C2, a transistor Q1, and a resistor R. A voltage Vcc is applied to one end 36 of the inductor L1. Another end 38 of the inductor L1 is connected to a node M. Also connected to the node M are a collector 40 of the transistor Q1 and one end 42 of the capacitor C1. Another end 44 of the capacitor C1 and an emitter 46 of the transistor Q1 are connected to a node N, as are one end 48 of the capacitor C2 and one end 50 of the resistor R. A second end 52 of the capacitor C2 and a second end 54 of the resistor R are grounded. (As used herein, the term 'ground' refers to a common or reference node, which may or may not be connected to main or building earth type grounds.) Bias current Ie, which flows across the resistor R, and a voltage VI at the node N are controlled by the feedback circuit 34.

The feedback circuit 34 has a peak detector 56, an error amplifier 58, and a low-pass filter 60. An input of the peak detector 56 is connected to the node M. The output of the peak detector 56 is fed into the error amplifier 58, which also receives a reference voltage as an input. The output of the error amplifier 58 is fed into the low-pass filter 60, and the output of the low-pass filter is connected to the base 62 of the transistor Q1. The feedback circuit 34 keeps the oscillation amplitude of the oscillator 32 substantially constant by changing its bias current Ie to compensate for a variation in load conductance.

Load conductance can increase, for example, when a resonant frequency of a PIT tag 12 is equal to or at least near the resonant frequency of the oscillator 32, and the PIT tag is positioned close enough to the locator circuit 30 so as to electromagnetically couple with the inductor L1. The inductor L1 serves as the search coil 20 in the locating apparatus 14 of FIGS. 1A-1B, which may include the locator circuit 30. An increase in load conductance will cause an increase in output of the error amplifier 58 and the low-pass filter 60, as well as an increase in the current Ie and the voltage VI.

Furthermore, it should be understood that other variations of the locator circuit 30 can be implemented, as is known to those skilled in the art. An advantage of the locator circuit 30 is that it is easily adapted to a dual or multiple frequency operation mode and/or to locating of both HDX and FDX PIT tags 12.

It will be apparent to one versed in the art that other oscillator configurations and/or other active devices (for example, field effect transistors) could be used in place of oscillator 32 without altering the scope or nature of the invention.

The oscillator 32 may or may not operate at a power level capable of causing the PIT tag 12 to transmit a message in a response signal. The message can include information such as a tag identification number identifying the PIT tag 12. However, since no response from the PIT tag 12 is needed to locate the PIT tag by using locator circuit 30, the oscillator 32 may be driven by using a small amount of power. Driving the oscillator 32 at this reduced power level advantageously increases battery life and reduces potential interference with other electronic equipment.

Figure 3:
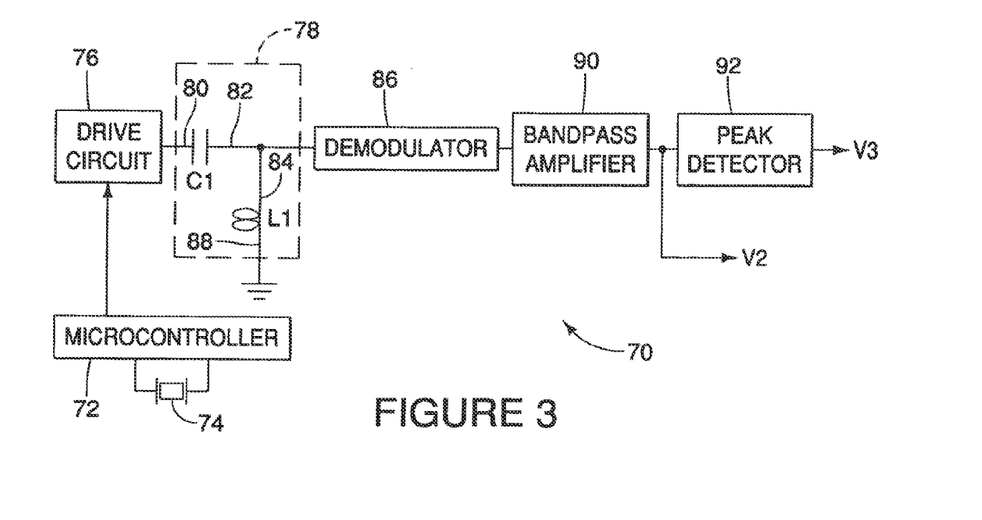
FIG. 3 is a block diagram of another exemplary circuit used in the PIT tag locating apparatus of FIG. 1B.

Referring now to FIG. 3, a second example of a PIT tag locator circuit is generally designated 70. Locator circuit 70 is less susceptible to error due to electromagnetic coupling to metal objects other than PIT tags. Additionally, locator 70 is less affected by variations in load conductance caused by temperature changes in the inductor. The location range of locator circuit 70 is also larger than that of locator circuit 30. In this example, a microcontroller 72 uses a crystal 74 to generate a drive frequency that is selected to match the resonance frequency of a PIT tag 12. Further, it is contemplated that PIT tags of different resonant frequencies could be used with different selected drive frequencies to detect multiple embedded PIT tags. The output of the microcontroller 72 is provided as an input to a drive circuit 76, which drives a resonator 78 (shown in dashed lines) formed by a capacitor C1 and an inductor L1 at a power level sufficient to excite a response from the PIT tag 12. The output of the drive circuit 76 is connected to one end 80 of the capacitor C1. A second end 82 of the capacitor C1 is connected to one end 84 of the inductor L1 and an input of a demodulator 86. Another end 88 of the inductor L1 is grounded. The output of the demodulator 86 is fed into a bandpass amplifier 90. The output of the bandpass amplifier 90, designated V2, is fed into an analog peak detector 92. The output of the peak detector 92 is designated V3. It should be noted that while a free-running oscillator is also contemplated for use with the present locator circuit 70, the described crystal-controlled drive frequency locator circuit is preferred because it provides an improved signal-to-noise ratio. It will also be apparent to one versed in the art that a drive circuit could function without the aid of the microcontroller 72. However, in some locator apparatuses, the microcontroller 72 may also be used to analyze the signals V2 and V3, and to control audio and/or visual display devices, as discussed herein in relation to the examples shown in FIGS. 5, 8 and 9.

When the resonator 78 in the locator circuit 70 is driven at a sufficient power, a signal, such as an interrogating signal, is output via the inductor L1. In response to the interrogating signal, a PIT tag 12 that is electromagnetically coupled with the resonator 78 transmits a response signal, which includes a message. When received by the locator circuit 70, the response signal is superimposed over the interrogating signal, which is held in the resonator 78. The demodulator 86 is configured to demodulate the signal held in the resonator 78. For PIT tags conforming to the ISO standard with a resonance frequency of 134.2 kHz, the demodulated response signal has a frequency of approximately 4.2 kHz.

Next, the response signal is separated from other components of the demodulator output by using the band-pass amplifier 90, and the response signal V2 is output to the peak detector 92. An amplitude peak value V3 is extracted from the demodulated response signal using the peak detector 92. Alternatively, the amplitude peak value can be determined from the output signal V2. Regardless of which of the output signals V2 and V3 is used, the peak amplitude can be calculated. The peak amplitude is related to the distance D between the inductor L1, which functions as the search coil 20 in a locating apparatus 14 that includes the locator circuit 70, and a PIT tag 12 that is electromagnetically coupled with the resonator 78. It is contemplated that a tag ID number can be included in the message to identify the PIT tag 12. The message can optionally be extracted and analyzed and the tag number determined using the signal V2.

Figure 4:
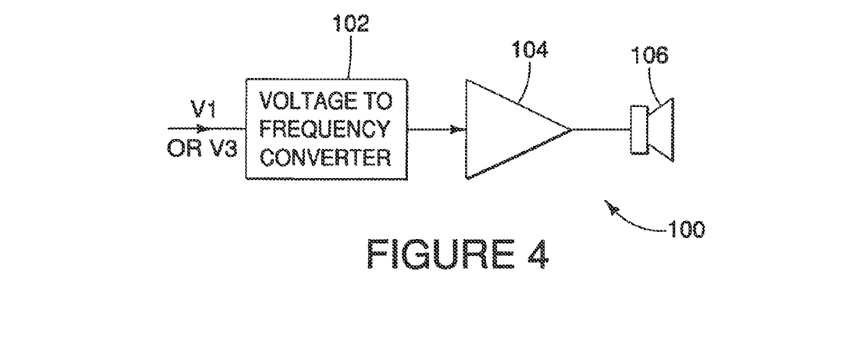
FIG. 4 is a block diagram of an audio indicator circuit for use with the circuits shown in FIGS. 2 and 3.

FIG. 4 shows an example of an audio indicator 100 that can be implemented with either of the above-described locator circuits 30, 70 to indicate the proximity of a PIT tag 12. Using the audio indicator 100, the voltage output from the first or second examples (i.e., V1 or V3) is input into a voltage-to-frequency converter 102. The voltage-to-frequency converter 102 converts the provided voltage into a frequency that will produce an audible tone. The frequency produced by the voltage-to-frequency converter 102 increases as the distance between the inductor L1 and the PIT tag decreases. Thus, the audible tone can also be configured to increase in pitch to provide feedback to the user as the distance decreases between the search coil 20 and the PIT tag 12. In particular, the frequency, and thus the pitch of the audible tone, will be at a maximum when the PIT tag 12 is directly below the center axis Z of the inductor L1.

FIG. 4 further shows the output of the voltage-to-frequency converter 102 being fed into an amplifier 104, and then into a loudspeaker or headphone 106 to provide the audible tone. Advantageously, the lateral position of the PIT tag 12 (i.e., the position directly above where the PIT tag is implanted) can accurately be determined by locating the position on the specimen's skin that corresponds to the highest-frequency audible tone. Additionally, the distance of the PIT tag from the surface of the skin (i.e., the depth that the PIT tag was implanted) can be estimated from the pitch of the audible tone when the lateral position has been determined.

Figure 5:
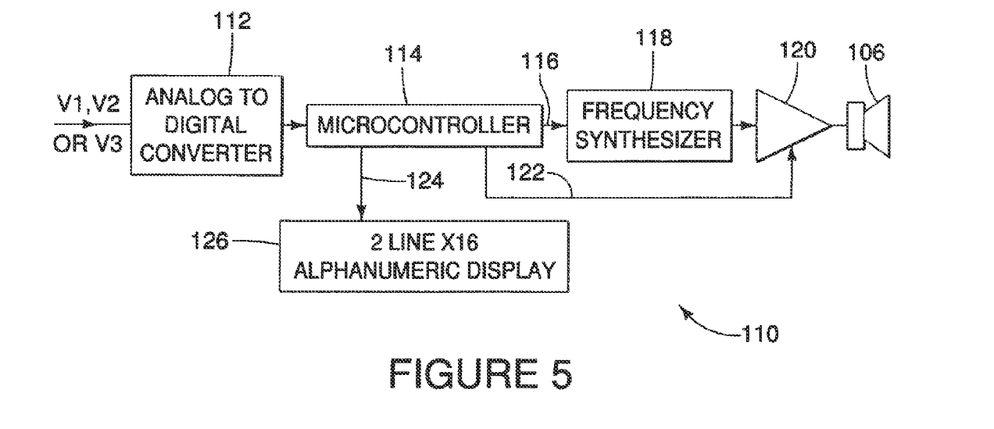
FIG. 5 is a block diagram of an audiovisual indicator circuit for use with the circuits shown in FIGS. 2 and 3.

FIG. 5 shows an example of an audiovisual indicator 110 that can be used with either the first or second embodiment locator circuits 30, 70. The indicator 110 receives as an input a voltage signal (V1, V2, or V3) having an amplitude that is non-linearly related to the distance between the search coil 20 and a PIT tag 12 that is electromagnetically coupled to the search coil. The input signal is digitized using an analog-to-digital converter 112. The output of the analog-to-digital converter 112 is input into a microcontroller 114. The microcontroller 114 processes the output from the analog-to-digital converter 112 to provide a binary output signal that is linearly related to the distance between the search coil 20 and the PIT tag 12. Thereafter, a first output 116 of the microcontroller 114 is input into a frequency synthesizer 118, which converts the output of the microcontroller into a signal that can be used to generate an audible tone. The audible tone provides distance data similar to that discussed above with respect to FIG. 3. The frequency synthesizer 118 preferably converts the output of the microcontroller 114 to one of a multitude of distinct tones (e.g., one of 48 distinct tones spanning four octaves) that are used to indicate the distance D between the search coil 20 and the electromagnetically coupled PIT tag 12. One output from the frequency synthesizer 118 is amplified by an amplifier 120. A second output 122 from the microcontroller 114 is used to control the gain of the amplifier 120. The amplified signal output from the amplifier 120 is input to a loudspeaker 106, which provides an audible tone to a user.

Additionally, a third output 124 of the microcontroller 114 can be fed into an alphanumeric display 126, which may be but is not limited to a 2-line by 16 character display. One line of the display 126 is configured to display a bar-graph, which may conveniently contain 48 bars for a 16-character display, and another line of the display is configured to show a corresponding range scale in, for example, centimeters. The length of the bar-graph increases as the distance D between the search coil 20 and the PIT tag 12 decreases. The bar-graph type display 126 can provide a user with a visual indication of the vertical position of the PIT tag 12 (i.e., the distance the PIT tag was implanted into the specimen) once the lateral position of the PIT tag has been determined, and the inductor L1 in the resonator 32, 78 is centered above the electromagnetically coupled PIT tag. In this position the length of the bar-graph will be a maximum. Of course, other visual display types are also contemplated and capable of being implemented with the output 124 of the microcontroller 114.

Figure 6:
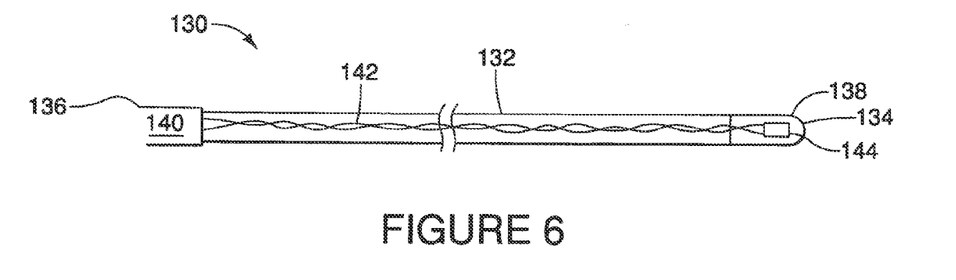
FIG. 6 is a cross-sectional view of a search probe for use with the PIT tag locating apparatus of FIG. 1B.

Sometimes a PIT tag 12 is implanted in an area where the specimen's skin is irregular or not generally flat. In such circumstances, it may be difficult to accurately determine the lateral position of the PIT tag 12 using the search coil 20. Instead, a pencil-shaped probe 130 as shown in FIG. 6 may be used to locate a PIT tag 12. The probe 130 is generally formed from a relatively long and thin cylindrical tube 132 configured for insertion into a specimen and having a first end 134 and a second end 136. The tube 132 may be made of any durable material that will not adversely react with the specimen, such as plastic or stainless steel, and preferably has an outer diameter of about 4.8 mm and a length of about 150-200 mm. The first end 134 of the tube 132 is capped by a plastic cap 138, and the second end 136 of the tube 132 is fitted with a cable or connector 140 so that the probe 130 can be connected to the processing and display unit 18. The interior of the probe 130 has a small coil 144, which is preferably but not necessarily ferrite-cored, disposed within the plastic cap 138. The coil 144 functions as a search coil similar to the search coil 20 of FIG. 1B. The coil 144 can output a signal to the processing and display unit 18 via lead wires 146 and connector 140 located at the second end 136 of the tube 132.

To use the probe 130, an approximate lateral location of the PIT tag 12 is first determined using the search coil 20. A small incision is made in the specimen at this location, and the probe 130 is inserted therein. The probe 130 may then be manipulated within the incision to determine the shortest distance between the PIT tag 12 and the coil 144. It should be noted that because of the relative size difference between the coil 144 used within the probe 130 and the search coil 20, the range of the probe is less than that of the search coil.

Figure 7A:
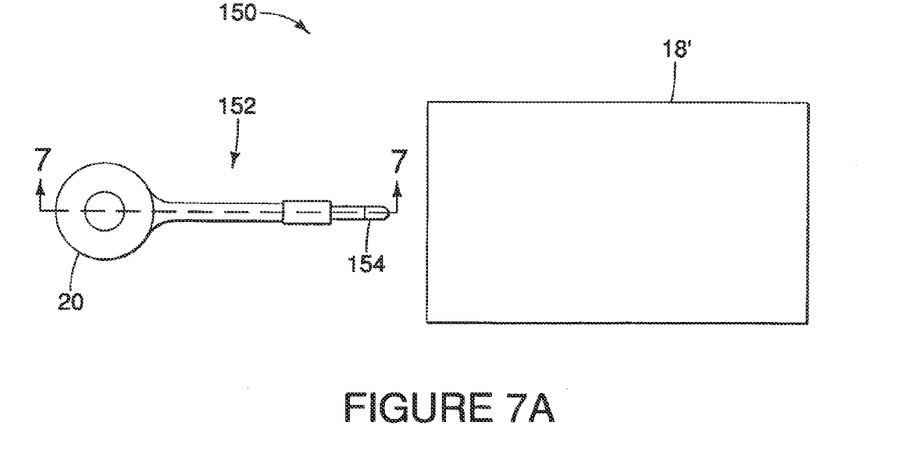
FIG. 7A is an overhead plan view of another embodiment of a PIT tag locating apparatus including a rotatable search coil.
Figure 7B:
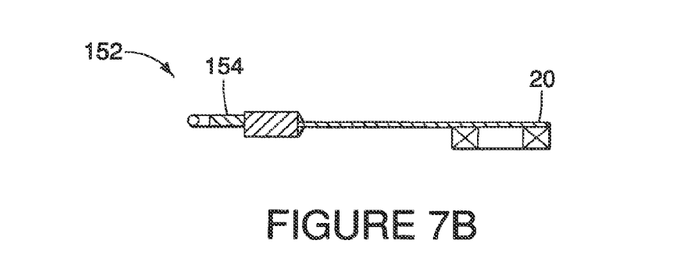
FIG. 7B is a cross-sectional view of the rotatable search coil assembly of FIG. 7A along the line 7-7.

If the orientation of the search coil 20 is fixed relative to the processing and display unit 18, it may be difficult or inconvenient to read the bar graph from the display window 24 of the processing and display unit while the search coil is positioned against the specimen. In such situations, a rotatable search coil is advantageous. FIGS. 7A and 7B show another embodiment of a PIT tag locating apparatus 150 including a rotatable coil assembly 152 for use with the circuits of FIGS. 2 and 3. The rotatable coil assembly 152 has a search coil 20 disposed on a first end of the rotatable coil assembly and a rotationally symmetrical plug 154 disposed on a second end of the rotatable coil assembly.

The PIT tag locating apparatus 150 also includes a processing and display unit 18'. The processing and display unit 18' includes many of the same features as processing and display unit 18, but may also incorporate additional features, such as a female connector (not shown) configured to receive the plug 154, connecting the rotatable coil assembly 152 to the processing and display unit 18'.

The plug 154 of the rotatable search coil assembly 150 can be generally cylindrical in shape, and is axially aligned generally along a direction that is perpendicular to the center axis Z of the search coil 20. The plug 154, after being connected to the processing and display unit 18', preferably is freely rotatable about its alignment axis. This construction allows the rotatable coil assembly 152 to rotate freely about an axis that is generally perpendicular to the center axis Z of the search coil 20. The rotatable coil assembly 152 enables more convenient viewing of the processing and display unit 18' when scanning angled, irregular, or even downward-facing surfaces of specimens.

It may further be desirable to locate an implanted PIT tag 12 and read a tag identification number associated therewith. The signal V2 shown in FIG. 3 has a message which contains a binary tag identification number sequence along with header information and error-detection bits, as defined by ISO 11784 and 11785 standards. The signal V2 and message can be decoded using known techniques.

Figure 8:
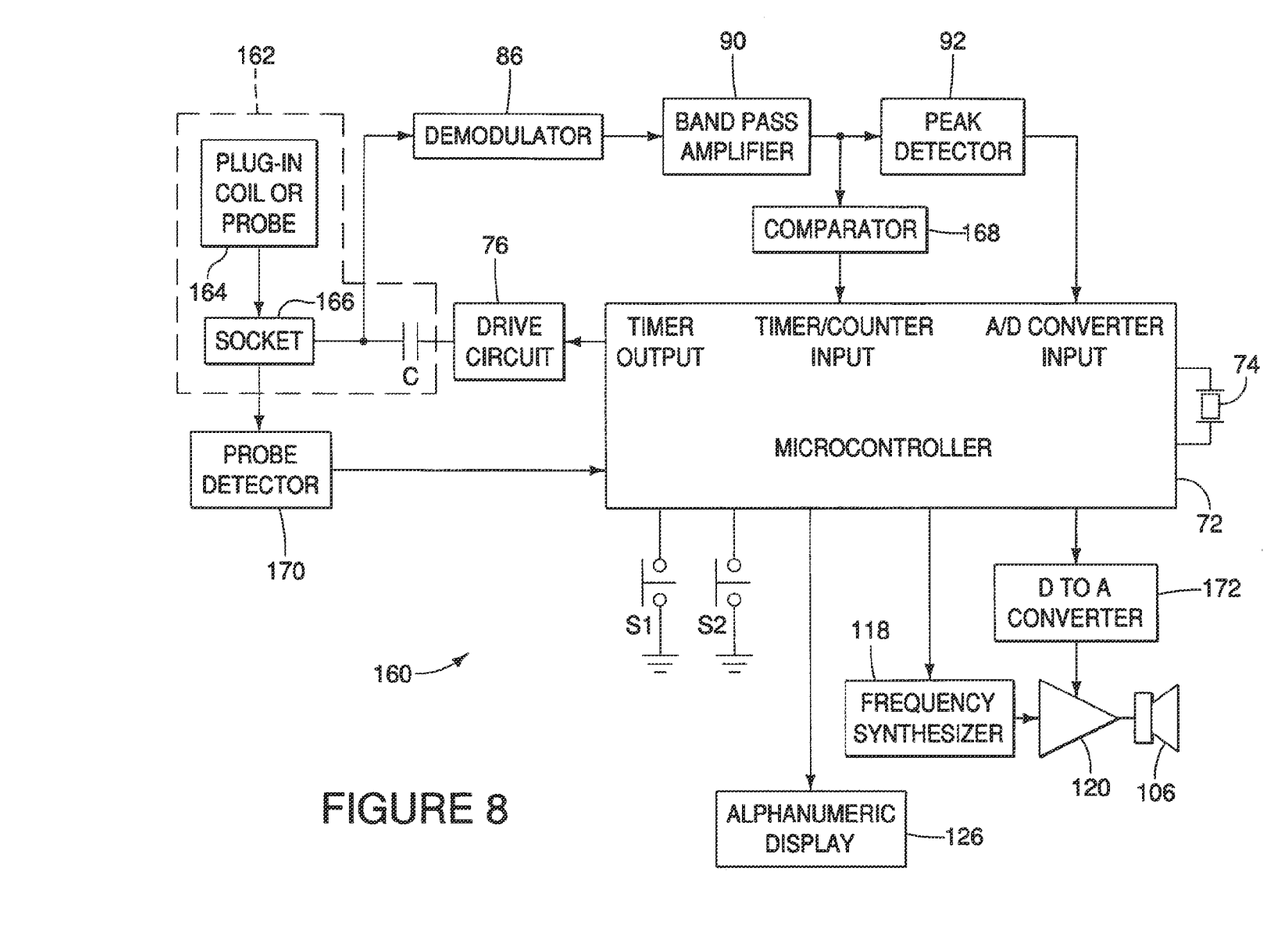
FIG. 8 is a block diagram of an apparatus capable of locating a PIT tag and reading an associated tag identification number.

Referring now to FIG. 8, a circuit 160 capable of FDX PIT tag location using the example locator circuit 70, reading a decoded tag identification number, and automatic detection of the probe is disclosed. This example generally combines the locator circuit 70 and the audiovisual indicator 110, and components shown in FIG. 8 are designated with the same reference numbers as similar components shown in FIGS. 3 and 5.

As described above, the microcontroller 72 uses the crystal 74 to control a drive frequency selected to match a resonance frequency of a selected PIT tag 12. The drive frequency of the present embodiment is derived from a timer output of the microcontroller 72. However, other methods of obtaining the drive frequency are contemplated, such as by using a frequency synthesizer. An output of the microcontroller 72 is input into a drive circuit 76 that drives a resonator 162 (shown in dashed lines) formed from the capacitor CI and a plug-in coil or probe 164 connected to the circuit 160 via a socket 166. The output of the drive circuit 76 is connected to one end of the capacitor C1. The other end of the capacitor C1 is connected to the socket 164 and the demodulator 86.

The resonator 162 is driven at a particular frequency and with enough power to generate an interrogation signal that excites a response from the PIT tag 12 when electromagnetic coupling between the resonator 162 and the PIT tag 12 occurs. The response signal generated by the PIT tag 12 is superimposed onto the interrogating signal across the resonator 162, and is demodulated by the demodulator 86. A bandpass amplifier 90 receives the output of the demodulator 86 which includes the interrogating signal as an input, and separates the interrogating signal from the response signal, as in FIG. 3. The response signal is provided as the output of the bandpass amplifier 90, and is input into both a comparator 168 that converts the response signal to logic levels suitable for the microcontroller interface and a peak detector 92. The output of the comparator 168 includes the tag identification number transmitted by the PIT tag 12 in its response signal. The output of the peak detector 92 is a voltage that is related to the distance D between the PIT tag 12 and the coil or probe 164.

A probe detector 170 detects whether the search coil 20 or the probe 130 is connected to the circuit 160 via the socket 166. In another embodiment (not shown) the search coil may be fixed, as in FIGS. 1A and 1B, and only the probe 130 attached using a plug and socket. The output of the probe detector 170 is provided to the microcontroller 72 so that the microcontroller can properly interpret received data.

Additionally, the microcontroller 72 is connected to two switches S1, S2. The switches allow a user to adjust settings such as audio tone amplitude, and display backlight level. The switches S1, S2 can also cause the locating apparatus 14 to read, store, and display the tag identification number of a detected PIT tag that is within range of the locating apparatus. If no PIT tag 12 is within an operating range (i.e., capable of electromagnetically coupling with the coil or probe 164), the switches S1, S2 may have the alphanumeric display 126 show previously-stored tag identification numbers. Microcontroller flash memory or an external EEPROM, for example, may be used to store tag identification numbers and selected audio and/or backlight levels.

The microcontroller 72 also provides an output to a frequency synthesizer 118 to generate a tone that is related to the distance D between the PIT tag 12 and the search coil 20. The output of the frequency synthesizer 118 is input into an amplifier 120. Another output of the microcontroller 72 is fed into a digital-to-analog converter 172. The digital-to-analog converter 172 connects to the amplifier 120, and sets the gain of the amplifier. The output of the amplifier 120 is provided to a loudspeaker 106, which creates an audible tone as an indication of the distance D between the PIT tag 12 and the coil or probe 164 to a user. The microcontroller 72 also outputs another signal to the alphanumeric display 126 which can display a bar graph and scale similar to that described above with respect to FIG. 5.

Figure 9:
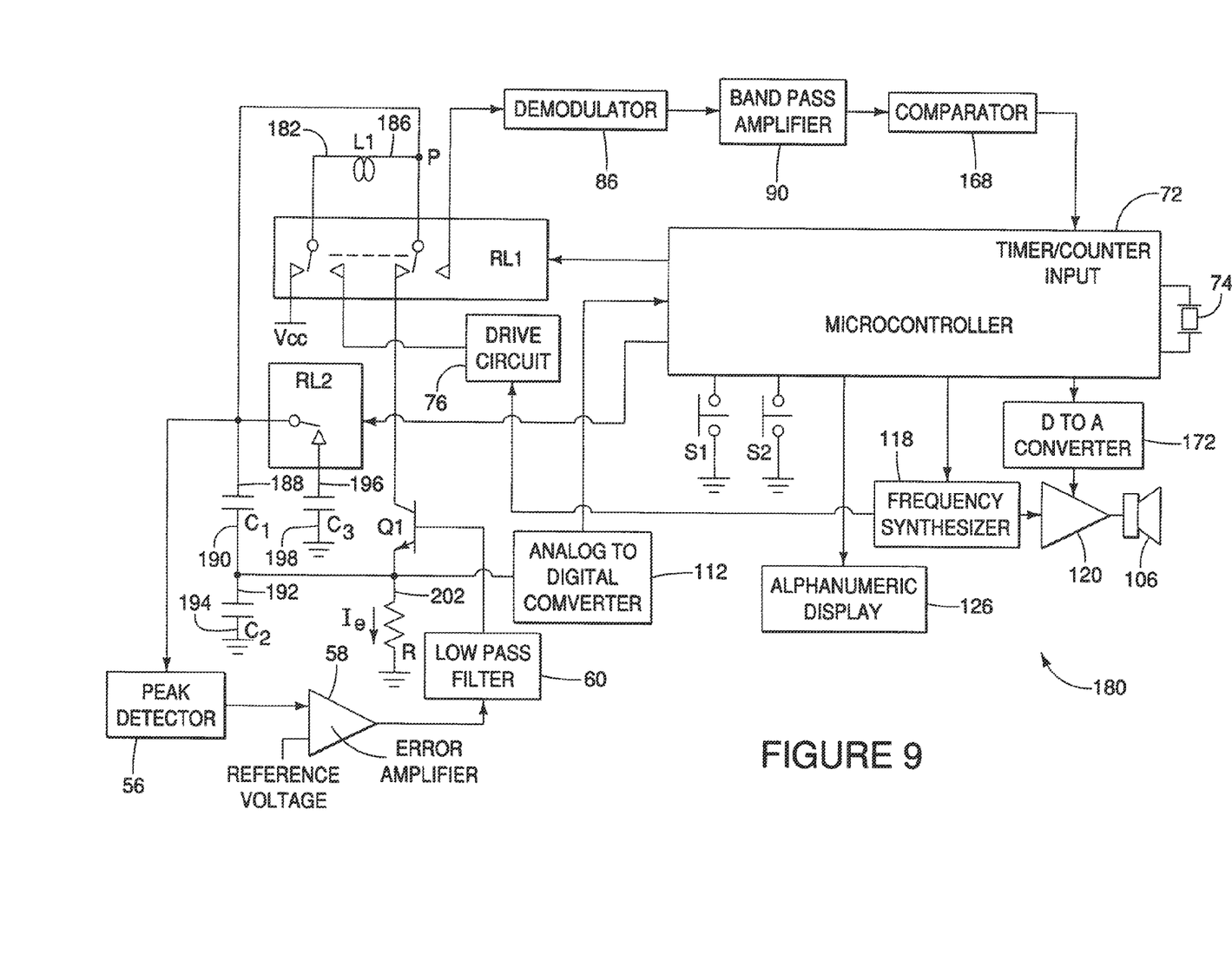
FIG. 9 is a block diagram of an apparatus for locating a PIT tag and capable of switching frequencies to operate at frequencies of 125 kHz and 134.2 kHz.

Although the location circuits described in these examples have some response to PIT tags of a different resonant frequency from that to which they are tuned, improved lateral position sensitivity and depth determination occurs when the location circuit and the PIT tag have the same resonant frequency. FIG. 9 shows one embodiment of a circuit generally designated 180 that can be tuned to either a 125 kHz or 134.2 kHz resonant frequency PIT tag, and also can read the identification numbers of FDX ISO 134.2 kHz PIT tags. FIG. 9 has similar components of the examples described in FIGS. 1-8 identified with similar reference numerals.

To locate a PIT tag 12, a microcontroller 72 controls a relay RL1 such that one end 182 of an inductor L1 is connected to the voltage Vice and the collector of a transistor Q1 is connected to node P. Another end 186 of inductor L1 is also connected to the node P, as is one end 188 of a capacitor C1. A second end 190 of the capacitor C1 is connected to both the emitter of a transistor Q1 and one end 192 of a capacitor C2. Another end 194 of capacitor C2 is grounded. Depending on the frequency of the PIT tag 12 a user is searching for, the microcontroller 72 may operate a relay RL2 such that one end 196 of an additional capacitor C3 is also connected to the node P. The other end 198 of the capacitor C3 is grounded. Increasing the capacitance by use of the capacitor C3 changes the resonant frequency of oscillation of the circuit 180.

A peak detector 56 is also connected to the node P. An output of the peak detector 56 is input into an error amplifier 58 and low-pass filter 60, and the output of the error amplifier and filter is provided to the base of the transistor Q1. In this configuration the operation of the circuit is as described in relation to FIG. 2, and the voltage at the end 202 of the resistor R is related to the distance between the inductor L1 (search coil 20) and the PIT tag 12. This voltage is connected to an analog to digital converter 112. The output of the analog to digital converter 112 is input into the microcontroller 72, which is controlled by the crystal 74. The microcontroller 72 produces outputs that are used to generate an audio tone and to drive an alphanumeric display 126 as described above in relation to FIG. 8.

In order to read a PIT tag 12 after it has been located, the microcontroller 72 controls the relay RL1 so that one end 182 of the inductor L1 is connected to a drive circuit, and the node P is connected to a demodulator 86. The microcontroller 72 also controls the frequency synthesizer 118 to output a signal to the drive circuit 76 for driving the resonator formed by L1, C1 and C2 at the predetermined resonant frequency. The resonator is driven at a power level such that an interrogating signal is generated and so that a PIT tag 12 will respond to the interrogating signal when in range (i.e., when the PIT tag is energized). The response signal from the PIT tag 12 is superimposed across the inductor L1 and capacitors C1, C2. The response signal, is demodulated and input to the microcontroller 72 as described in relation to FIG. 8. The microcontroller 72 then determines, displays, and stores the tag identification number from the response signal.

It should be noted that this embodiment uses the frequency synthesizer 118 to provide a timing signal for the driving circuit. This enables the drive frequency (or a plurality of drive frequencies) to be set independently of the crystal frequency, but it does require that audio tone indication be turned off momentarily while reading the PIT tag identification number. The overall power consumption of this embodiment is advantageously reduced, because for most of the time only the low-powered oscillator composed of Q1, L1, C1 and C2 is operating, and the high power drive circuit 76 is activated only for a brief interval to read the tag number. Additionally, it should be understood that features of the present embodiment can be incorporated into other embodiments.

Figure 10:
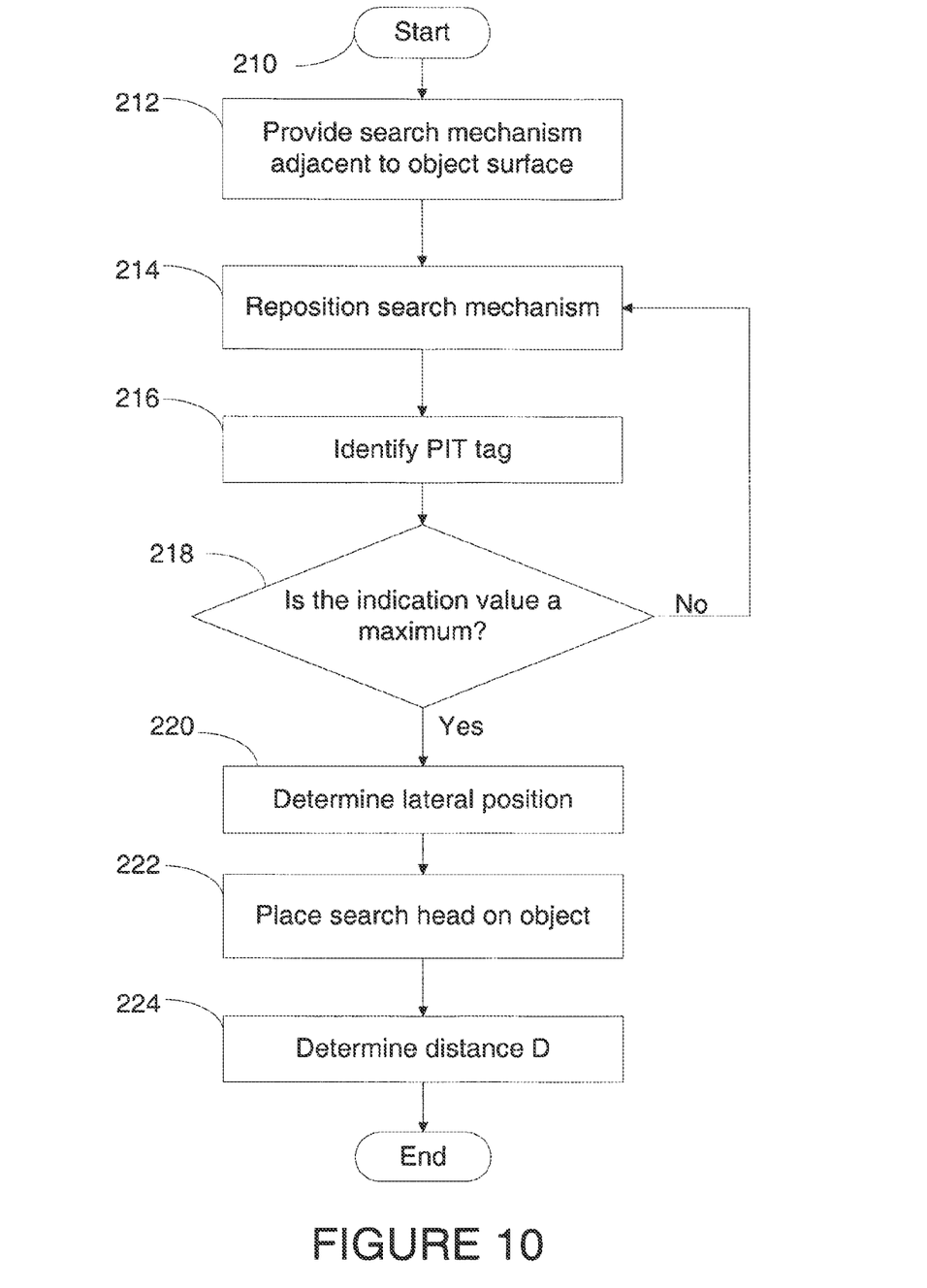
FIG. 10 is a flowchart illustrating an exemplary method of using the PIT tag locating apparatus of FIG. 1B.

Referring now to FIG. 10, an exemplary method 210 of using the PIT tag locating apparatus 14 is shown. The method 210 includes a step 212 of providing a search mechanism, such as the search coil 20, adjacent to the outer surface of the object 16 into which the PIT tag 12 is embedded.

Next, in step 214 the search mechanism is repositioned along the outer surface of the object, and a user notes the indication provided by either the audio indicator 100 or the audiovisual indicator 110. In step 216, the PIT tag locating apparatus 14 is used to identify the embedded PIT tag 12. For example, the PIT tag locating apparatus 14 may receive an identification number from the PIT tag 12.

In step 218, it is determined if the indication value from the indicator 100, 110 is a maximum. A maximum indication value indicates that the current position of the search mechanism corresponds to a minimum straight-line distance D between the search coil 20 and the PIT tag 12. The indication value is at a maximum value when, for example the pitch emitted by the indicator 100, 110 is highest, or when the display of the audiovisual indicator 110 indicates the shortest distance, for example by showing maximum length of a bar-graph.

If the indicator 100, 110 indicates a maximum value (i.e., if the position of the search coil 20 corresponds to a minimum distance D), the process proceeds to step 220. Otherwise, the process returns to step 214, and the search coil is repositioned, and a new indication value is obtained. This repositioning process continues until a maximum indication value is obtained.

In step 220 the lateral position of the embedded PIT tag 12 is determined. When the indication value reaches a maximum as determined in step 214, the lateral position of the PIT tag 12 is at the center of the search coil 20.

Next, at step 222, the search coil 20 is placed directly onto the outer surface of the object, with the lateral position of the PIT tag at the center of the search coil. The distance D between the search coil 20 and the PIT tag 12, which is the distance that the PIT tag 12 is embedded into the object, can be determined based upon one or both of the pitch of the audio tone from the indicator 100, 110, or the display of the audiovisual indicator 110 as discussed above in relation to FIGS. 4 and 5. In this way, a location of the PIT tag can be determined using the PIT tag locating apparatus 14. The lateral position of the PIT tag 12 may be marked through the hole in the search coil 20 using a suitable marking instrument.

While an embodiment of the invention has been described herein, it will be appreciated by those skilled in the art that changes, modifications and combinations of various example components may be made without departing from the invention in its broader aspects and as set forth in the following claims.

What is claimed is:

1. An apparatus comprising:
   a handheld device configured to determine a location for insertion of a probe in a body, wherein the location is determined in response to movement of the handheld device outside the body to identify one or more tags within the body; and
   a probe configured to move partially into an incision at the determined location of the body, the probe housing:
      a coil located at a distal terminal end of the probe, the probe composed of a durable material with the distal terminal end configured for temporary insertion into the incision and movable towards the one or more tags embedded in tissue of the body while a proximal end of the probe remains outside of the tissue of the body, wherein the coil inserted within the tissue of the body via the incision is configured to transmit a radio frequency signal resonating at a low frequency towards the one or more tags within the body, each tag configured to energize from the radio frequency signal and transmit a unique identifier encoded;
   wherein the apparatus determines position of the distal terminal end of the probe with reference to one or more tags within the body and provides an audible or visual indication of the determined position.

2. The apparatus of claim 1, further comprising:
   a depth calculation circuit configured to determine a distance between a particular tag within the body and the distal terminal end of the probe, the determination based at least on a signal received from the particular tag in response to receiving the low frequency signal transmitted from the coil.

3. The apparatus of claim 1, wherein the position of the probe comprises a distance to one or more tags within the body.

4. The apparatus of claim 1, wherein the position of the probe comprises a direction to one or more tags within the body.

5. The apparatus of claim 1, wherein the low frequency signal transmitted from the coil is a continuous signal.

6. The apparatus of claim 1, further comprising a switching circuit configured to adjust the resonant frequency of the coil.

\* \* \* \* \*